(12) United States Patent
Black et al.

(10) Patent No.: US 9,533,141 B2
(45) Date of Patent: Jan. 3, 2017

(54) ELECTRICAL STIMULATION LEADS AND SYSTEMS WITH ELONGATE ANCHORING ELEMENTS

(71) Applicant: Boston Scientific Neuromodulation Corporation, Valencia, CA (US)

(72) Inventors: James Robert Black, Medina, OH (US); David Ernest Wechter, Santa Clara, CA (US); Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/754,430

(22) Filed: Jun. 29, 2015

(65) Prior Publication Data

US 2016/0001060 A1 Jan. 7, 2016

Related U.S. Application Data

(60) Provisional application No. 62/021,607, filed on Jul. 7, 2014.

(51) Int. Cl.
*A61N 1/05* (2006.01)

(52) U.S. Cl.
CPC .................... *A61N 1/0558* (2013.01)

(58) Field of Classification Search
USPC ........................................ 607/128
See application file for complete search history.

(56) References Cited

U.S. PATENT DOCUMENTS

| 3,754,555 A | * | 8/1973 | Schmitt | A61N 1/375 607/128 |
| 3,814,104 A | * | 6/1974 | Irnich | A61N 1/375 607/128 |
| 4,112,952 A | * | 9/1978 | Thomas | A61N 1/0587 607/128 |

(Continued)

FOREIGN PATENT DOCUMENTS

| WO | 2004028618 | 4/2004 |
| WO | 2005028023 | 3/2005 |

(Continued)

OTHER PUBLICATIONS

U.S. Appl. No. 62/006,824, filed Jun. 2, 2014.

(Continued)

*Primary Examiner* — Kennedy Schaetzle
(74) *Attorney, Agent, or Firm* — Lowe Graham Jones PLLC; Bruce E. Black

(57) ABSTRACT

An electrical stimulation lead includes at least one lead body and at least one thin, elongate anchoring element. The lead body defines at least one anchoring lumen extending longitudinally along at least a portion of the lead body and at least one open slot in the lead body where each anchoring lumen is open at one of the at least one open slot. For each anchoring element, the first end of the anchoring element is disposed in one of the at least one anchoring lumen and the second end of the anchoring element is configured and arranged preferentially to extend out of the open slot associated with the anchoring lumen and away from the lead body in a deployed configuration unless the second end is constrained in a constrained configuration adjacent or within the lead body.

18 Claims, 9 Drawing Sheets

(56) References Cited

U.S. PATENT DOCUMENTS

| | | | |
|---|---|---|---|
| 4,280,512 A * | 7/1981 | Karr | A61N 1/0573 607/128 |
| 4,378,023 A * | 3/1983 | Trabucco | A61B 17/3468 607/120 |
| 4,706,682 A | 11/1987 | Stypulkowski et al. | |
| 4,913,147 A * | 4/1990 | Fahlstrom | A61N 1/057 607/2 |
| 5,052,407 A * | 10/1991 | Hauser | A61N 1/0587 607/125 |
| 5,179,962 A * | 1/1993 | Dutcher | A61N 1/0573 600/375 |
| 5,314,462 A * | 5/1994 | Heil, Jr. | A61N 1/0573 607/128 |
| 5,325,870 A * | 7/1994 | Kroll | A61N 1/0563 607/122 |
| 5,466,255 A * | 11/1995 | Franchi | A61N 1/0573 600/375 |
| 5,492,119 A * | 2/1996 | Abrams | A61N 1/0573 600/375 |
| 5,507,802 A * | 4/1996 | Imran | A61N 1/06 604/114 |
| 5,571,162 A * | 11/1996 | Lin | A61N 1/0573 607/122 |
| 5,609,623 A * | 3/1997 | Lindegren | A61N 1/05 607/126 |
| 5,674,273 A * | 10/1997 | Helland | A61N 1/05 604/175 |
| 5,868,741 A * | 2/1999 | Chia | A61B 18/1492 606/41 |
| 5,871,532 A * | 2/1999 | Schroeppel | A61N 1/0573 607/128 |
| 5,922,014 A * | 7/1999 | Warman | A61N 1/056 607/122 |
| 5,948,014 A * | 9/1999 | Valikai | A61N 1/056 607/122 |
| 5,957,966 A * | 9/1999 | Schroeppel | A61N 1/056 607/119 |
| 6,093,185 A * | 7/2000 | Ellis | A61B 18/1477 606/28 |
| 6,181,969 B1 | 1/2001 | Gord | |
| 6,249,708 B1 * | 6/2001 | Nelson | A61N 1/056 607/122 |
| 6,345,198 B1 * | 2/2002 | Mouchawar | A61N 1/056 600/374 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,671,544 B2 * | 12/2003 | Baudino | A61N 1/0551 607/117 |
| 6,741,892 B1 | 5/2004 | Meadows et al. | |
| 6,999,819 B2 | 2/2006 | Swoyer et al. | |
| 7,130,700 B2 * | 10/2006 | Gardeski | A61M 25/0021 600/585 |
| 7,187,983 B2 * | 3/2007 | Dahlberg | A61N 1/057 607/128 |
| 7,244,150 B1 | 7/2007 | Brase et al. | |
| 7,328,068 B2 | 2/2008 | Spinelli et al. | |
| 7,343,202 B2 | 3/2008 | Mrva et al. | |
| 7,369,894 B2 | 5/2008 | Gerber | |
| 7,437,193 B2 | 10/2008 | Parramon et al. | |
| 7,565,198 B2 | 7/2009 | Bennett et al. | |
| 7,672,734 B2 | 3/2010 | Anderson et al. | |
| 7,761,165 B1 | 7/2010 | He et al. | |
| 7,835,801 B1 * | 11/2010 | Sundararajan | A61N 1/0573 607/119 |
| 7,881,783 B2 | 2/2011 | Bonde et al. | |
| 7,899,550 B1 * | 3/2011 | Doan | A61N 1/0573 607/122 |
| 7,927,282 B2 * | 4/2011 | Hettrick | A61B 5/0215 600/375 |
| 7,949,395 B2 | 5/2011 | Kuzma | |
| 7,974,706 B2 | 7/2011 | Moffitt et al. | |
| 8,096,959 B2 * | 1/2012 | Stewart | A61B 17/00234 128/898 |
| 8,175,710 B2 | 5/2012 | He | |
| 8,224,450 B2 | 7/2012 | Brase | |
| 8,364,278 B2 | 1/2013 | Pianca et al. | |
| 8,452,420 B2 * | 5/2013 | Flach | A61N 1/057 606/213 |
| 8,469,954 B2 * | 6/2013 | Young | A61B 18/1477 600/466 |
| 8,532,789 B2 * | 9/2013 | Smits | A61N 1/05 607/119 |
| 2002/0151867 A1 * | 10/2002 | McGuckin, Jr. | A61B 18/00 604/506 |
| 2002/0156058 A1 * | 10/2002 | Borkan | A61N 1/05 514/177 |
| 2003/0195600 A1 | 10/2003 | Tronnes et al. | |
| 2004/0116992 A1 * | 6/2004 | Wardle | A61B 5/0215 607/116 |
| 2004/0230279 A1 * | 11/2004 | Cates | A61B 17/32006 607/126 |
| 2005/0288722 A1 | 12/2005 | Eigler et al. | |
| 2007/0043414 A1 * | 2/2007 | Fifer | A61N 1/0565 607/126 |
| 2007/0049980 A1 * | 3/2007 | Zielinski | A61B 5/0215 607/23 |
| 2007/0150036 A1 | 6/2007 | Anderson | |
| 2007/0293923 A1 * | 12/2007 | Soltis | A61N 1/056 607/122 |
| 2008/0103569 A1 * | 5/2008 | Gerber | A61N 1/05 607/115 |
| 2008/0103572 A1 | 5/2008 | Gerber | |
| 2008/0167701 A1 | 7/2008 | John et al. | |
| 2008/0183253 A1 | 7/2008 | Bly | |
| 2008/0183266 A1 * | 7/2008 | D'Aquanni | A61N 1/057 607/126 |
| 2009/0012592 A1 | 1/2009 | Buysman et al. | |
| 2009/0054949 A1 | 2/2009 | Alexander et al. | |
| 2009/0248095 A1 | 10/2009 | Schleicher et al. | |
| 2009/0254151 A1 | 10/2009 | Anderson et al. | |
| 2010/0131036 A1 | 5/2010 | Geistert et al. | |
| 2010/0168806 A1 | 7/2010 | Norlin-Weissenrieder et al. | |
| 2010/0256696 A1 * | 10/2010 | Schleicher | A61N 1/0558 607/2 |
| 2011/0251662 A1 * | 10/2011 | Griswold | A61N 1/37205 607/128 |
| 2012/0053665 A1 | 3/2012 | Stolz et al. | |
| 2012/0323253 A1 * | 12/2012 | Garai | A61N 1/057 606/129 |
| 2013/0066411 A1 | 3/2013 | Thacker et al. | |
| 2014/0330287 A1 * | 11/2014 | Thompson-Nauman | A61N 1/05 606/129 |
| 2014/0343645 A1 | 11/2014 | Wechter | |
| 2014/0343656 A1 | 11/2014 | Wechter | |
| 2015/0039069 A1 * | 2/2015 | Rys | A61N 1/0573 607/128 |
| 2015/0051616 A1 * | 2/2015 | Haasl | A61N 1/0573 606/129 |
| 2015/0246217 A1 | 9/2015 | Wechter | |

FOREIGN PATENT DOCUMENTS

| | | |
|---|---|---|
| WO | 2013082283 | 6/2013 |
| WO | 2015167800 | 11/2015 |

OTHER PUBLICATIONS

U.S. Appl. No. 14/726,233, filed May 29, 2015.
U.S. Appl. No. 62/111,596, filed Feb. 3, 2015.
U.S. Appl. No. 14/690,071, filed Apr. 17, 2015.

* cited by examiner

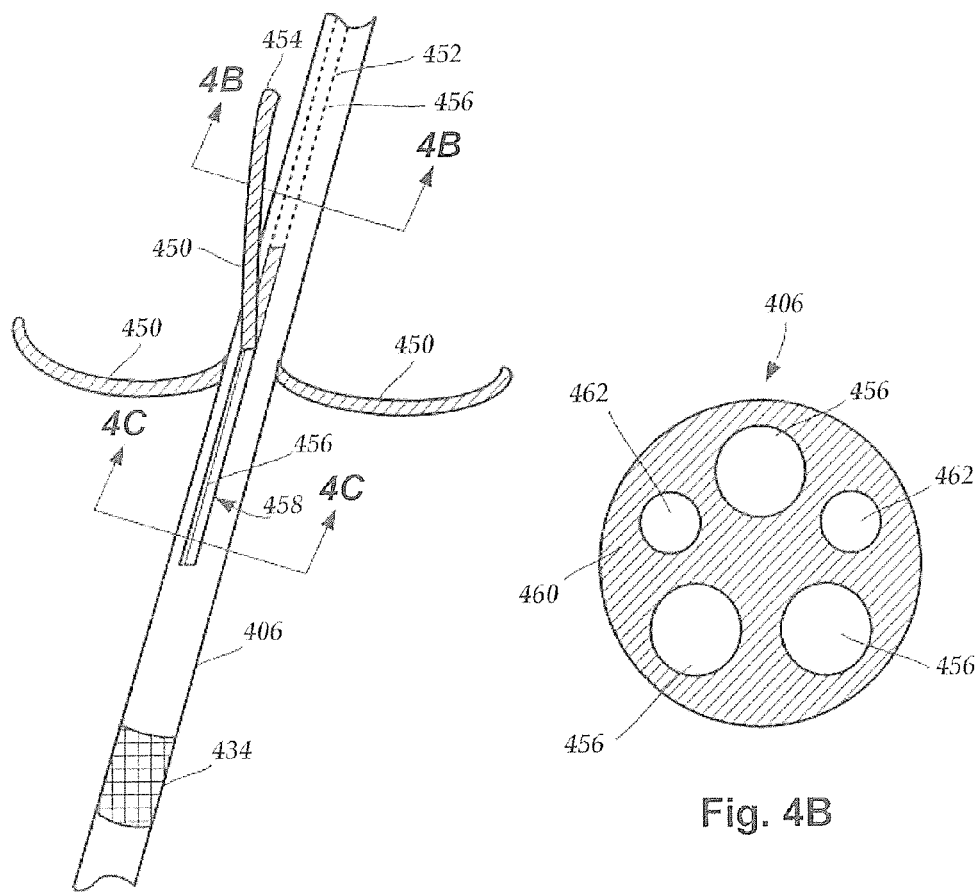
Fig. 4A
Fig. 4B
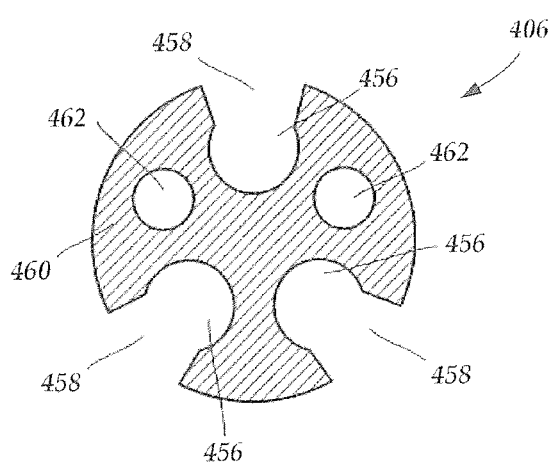
Fig. 4C

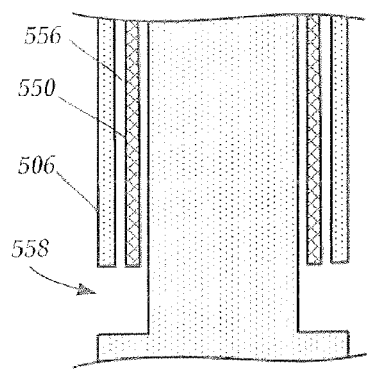 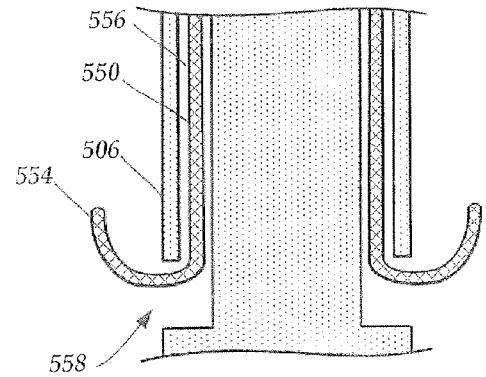
Fig. 5A  Fig. 5B
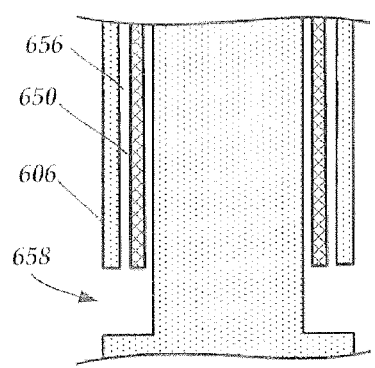 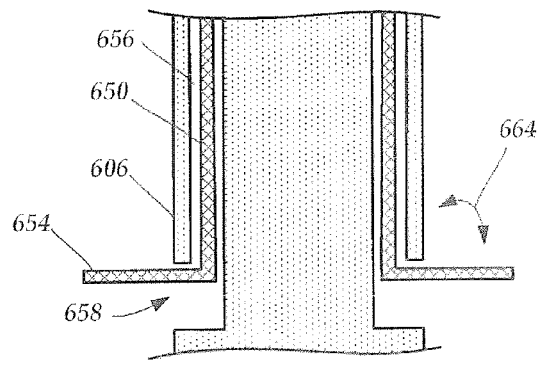
Fig. 6A  Fig. 6B

ELECTRICAL STIMULATION LEADS AND SYSTEMS WITH ELONGATE ANCHORING ELEMENTS

CROSS-REFERENCE TO RELATED APPLICATIONS

This application claims the benefit under 35 U.S.C. §119 (e) of U.S. Provisional Patent Application Ser. No. 62/021,607, filed Jul. 7, 2014, which is incorporated herein by reference.

FIELD

The present invention is directed to the area of implantable electrical stimulation systems and methods of making and using the systems, and in particular implantable electrical stimulation leads having elongate anchoring elements and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead including at least one lead body having a distal end portion, a proximal end portion, and a longitudinal length; at least one electrode disposed along the distal end portion of the at least one lead body; at least one terminal disposed along the proximal end portion of the at least one lead body; at least one conductor electrically coupling the at least one terminal to the at least one electrode; and at least one thin, elongate anchoring element having a first end and a second end. The lead body defines at least one anchoring lumen extending longitudinally along at least a portion of the lead body and at least one open slot in the lead body where each anchoring lumen is open at one of the at least one open slot associated with the anchoring lumen. For each anchoring element, the first end of the anchoring element is disposed in one of the at least one anchoring lumen and the second end of the anchoring element is configured and arranged preferentially to extend out of the open slot associated with the anchoring lumen and away from the lead body in a deployed configuration unless the second end is constrained in a constrained configuration adjacent or within the lead body.

In at least some embodiments, in the deployed configuration, each of the at least one anchoring element forms a hook. In at least some embodiments, in the deployed configuration, each of the at least one anchoring element forms a tine extending straight out of the anchoring lumen. In at least some embodiments, in the deployed configuration, each of the at least one anchoring element extends perpendicularly from the lead body. In at least some embodiments, in the deployed configuration, each of the at least one anchoring element extends at an angle in a range of 10 to 170 degrees relative to the lead body. In at least some embodiments, the anchoring lumen and open slot are configured and arranged to permit the anchoring element to lie down within the anchoring lumen when constrained. In at least some embodiments, the lead also includes a mechanism coupled to the at least one anchoring element and configured and arranged to permit a user to retract the at least one anchoring element into the at least one anchoring lumen. In at least some embodiments, in the deployed configuration, the first end is disposed within the anchoring lumen proximal to the open slot. In at least some embodiments, in the deployed configuration, the first end is disposed within the anchoring lumen distal to the open slot. In at least some embodiments, the lead body includes a multi-lumen tubing defining the at least one anchoring lumen and one or more conductor lumens.

Another embodiment is an electrical stimulation lead including at least one lead body having a distal end portion, a proximal end portion, and a longitudinal length; at least one electrode disposed along the distal end portion of the at least one lead body; at least one terminal disposed along the proximal end portion of the at least one lead body; at least one conductor electrically coupling the at least one terminal to the at least one electrode; and at least one thin, elongate anchoring element having a first end and a second end. Each anchoring element is wrapped around the lead body with the first and second ends extending away from the lead body. The anchoring element is configured and arranged to be constrained with the first and second ends lying against the lead body.

In at least some embodiments, each anchoring element is formed of a superelastic material that preferentially assumes a deployed configuration with the first and second ends extending away from the lead body unless constrained. In at least some embodiments, unless constrained, the first and second ends of each anchoring element extend perpendicularly relative to the lead body. In at least some embodiments, each anchoring element forms at least one coil around the lead body.

Yet another embodiment is an electrical stimulation lead including at least one lead body having a distal end portion, a proximal end portion, and a longitudinal length; at least one electrode disposed along the distal end portion of the at least one lead body; at least one terminal disposed along the proximal end portion of the at least one lead body; at least one conductor electrically coupling the at least one terminal to the at least one electrode; and at least one thin, elongate anchoring element having a first end and a second end. The lead body defines at least one anchoring lumen extending longitudinally along at least a portion of the lead body and at least one open slot in the lead body. Each anchoring lumen is open at one of the at least one open slot associated with the anchoring lumen. For each anchoring element, the first end of the anchoring element is disposed in one of the at least one anchoring lumen and the second end of the anchoring element is configured and arranged preferentially to extend out of the open slot associated with the anchoring lumen and away from the lead body in a deployed configuration. The first end is disposed within the anchoring lumen proximal to the open slot In at least some embodiments, each anchoring element is formed of a superelastic material. In at least some embodiments, unless constrained, the second end of each anchoring element extends at an angle in a range from 10 to 170 degrees relative to the lead body. In at least some embodiments, the lead is configured and arranged for retraction of the at least one anchoring element by application of at least a predetermined amount of pulling force to the lead when the lead is implanted.

A further embodiment is an electrical stimulating system including any of the electrical stimulation leads described above; and a control module coupleable to the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of a portion of one embodiment of a lead with anchoring elements, according to the invention;

FIG. 4B is a schematic lateral cross-sectional view of one embodiment of a multi-lumen tubing of the lead of FIG. 4A taken at line 4B-4B, according to the invention;

FIG. 4C is a schematic lateral cross-sectional view of one embodiment of a multi-lumen tubing of the lead of FIG. 4A taken at line 4C-4C, according to the invention;

FIG. 5A is a schematic longitudinal cross-sectional view of a portion of one embodiment of a lead with anchoring elements, according to the invention;

FIG. 5B is a schematic longitudinal cross-sectional view of the portion of the lead of FIG. 5A with the anchoring elements deployed, according to the invention;

FIG. 6A is a schematic longitudinal cross-sectional view of a portion of one embodiment of a lead with anchoring elements, according to the invention;

FIG. 6B is a schematic longitudinal cross-sectional view of the portion of the lead of FIG. 6A with the anchoring elements deployed, according to the invention;

DETAILED DESCRIPTION

The present invention is directed to the area of implantable electrical stimulation systems and methods of making and using the systems, and in particular implantable electrical stimulation leads having elongate anchoring elements and methods of making and using the leads.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036 all of which are incorporated by reference.

Figure 1:
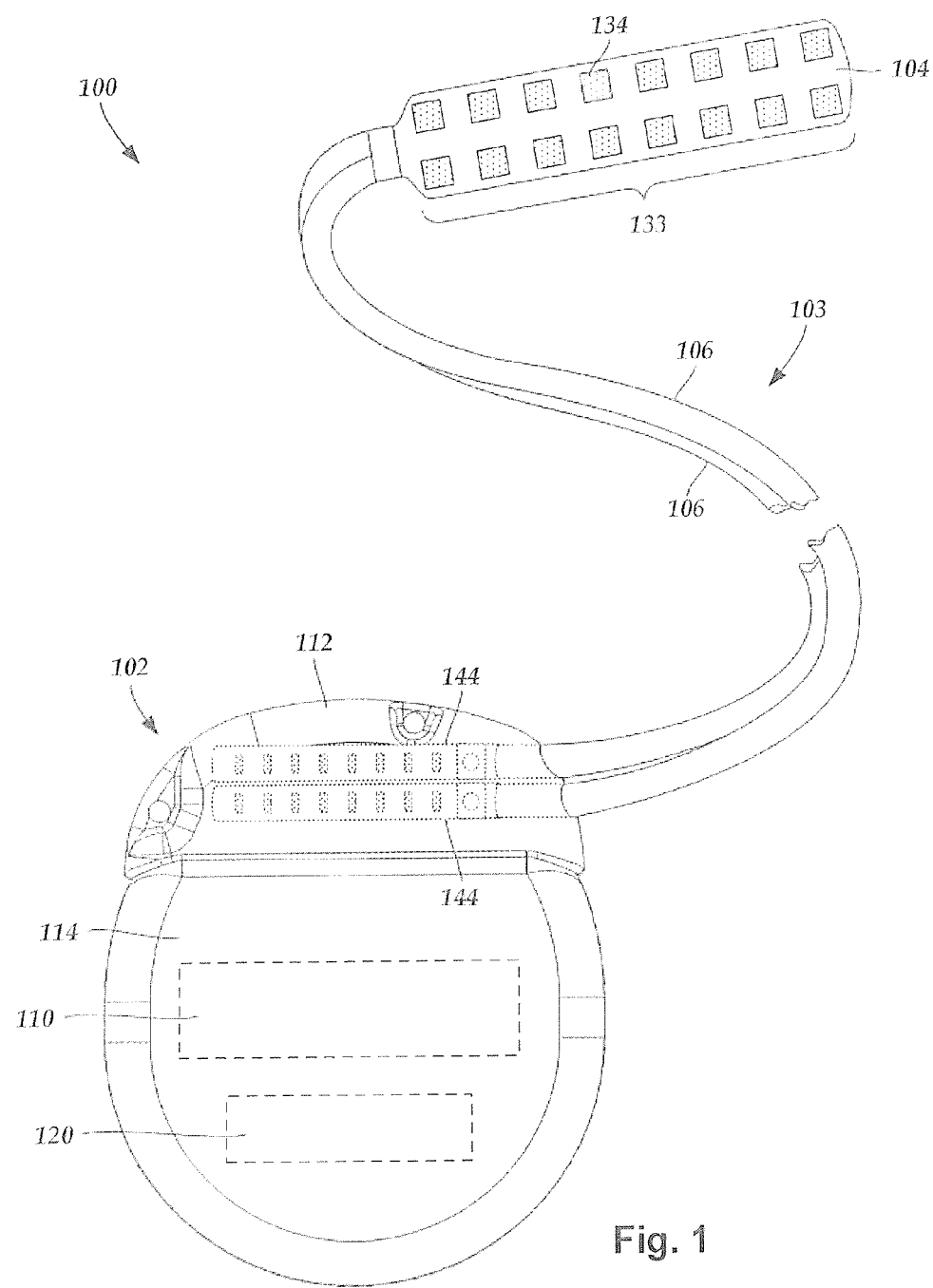
FIG. 1 is a schematic front view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106. In some embodiments, there may be a single electrode 134 or a single terminal.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
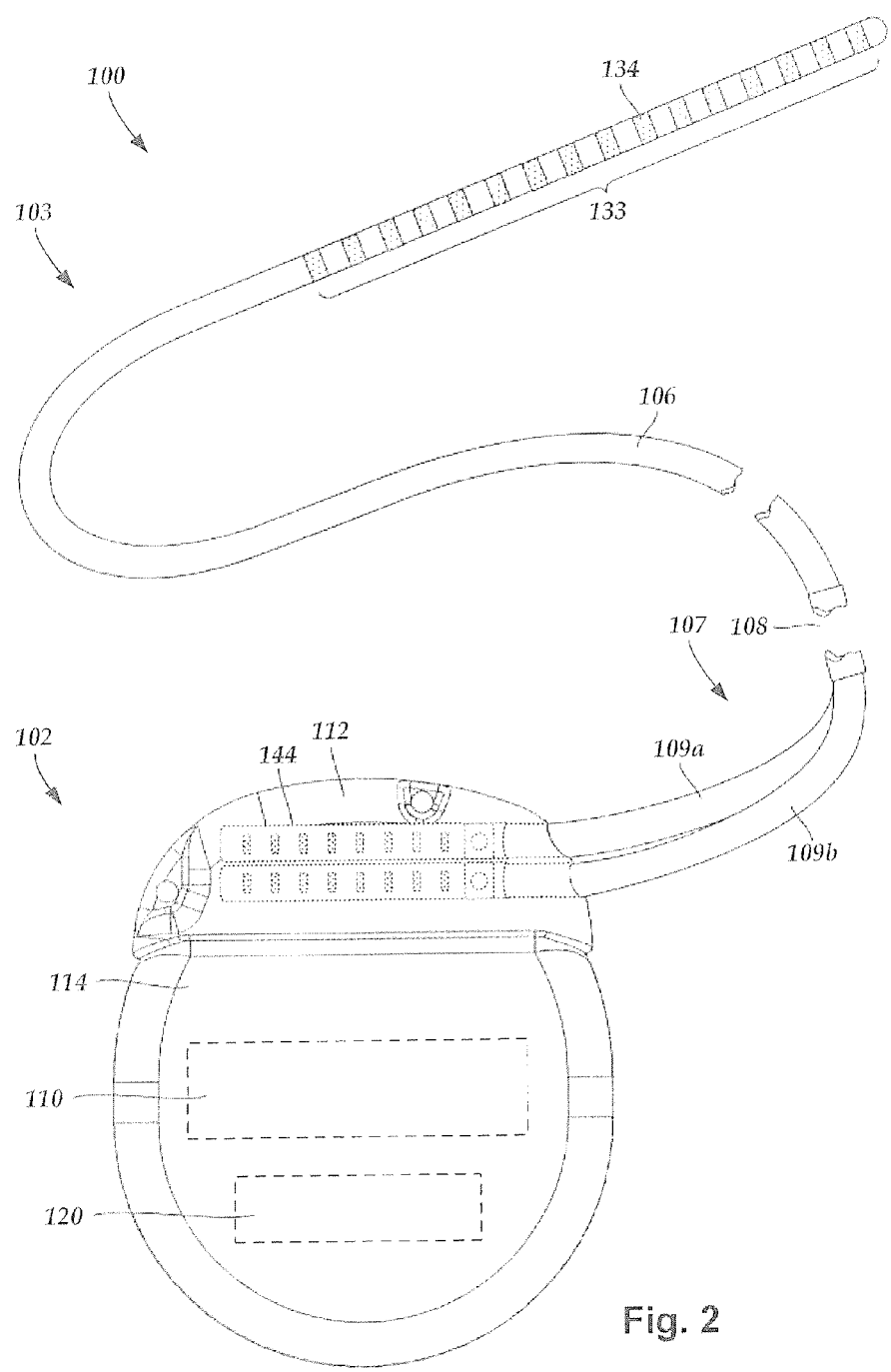
FIG. 2 is a schematic front view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 33). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of one or more lead extensions including, for example, a splitter, an adaptor, or the like or combinations thereof it will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
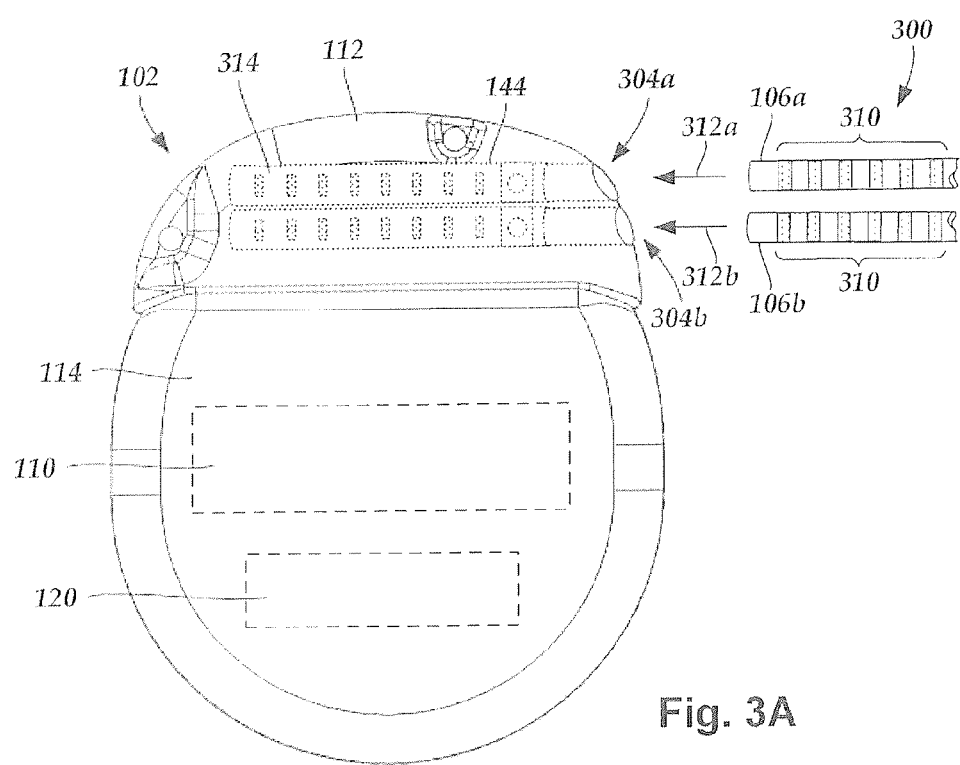
FIG. 3A is a schematic front view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
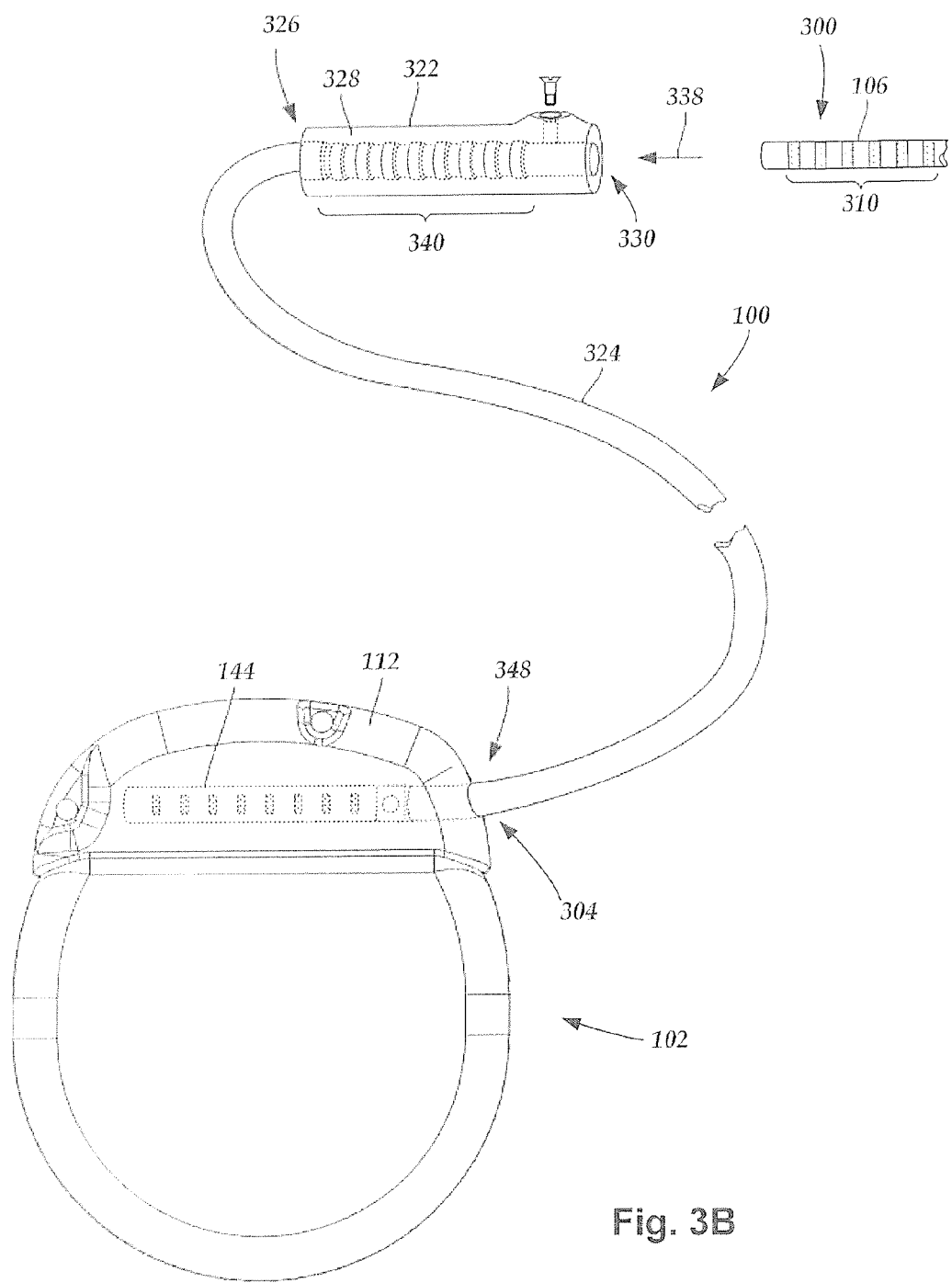
FIG. 3B is a schematic front view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Lead anchoring elements can be attached to the lead to facilitate anchoring the lead into patient tissue. The term "tissue" includes, but is not limited to, muscular tissue, connective tissue, organ tissue, bone, cartilage, nerve tissue, and the like. These lead anchoring elements, as opposed to conventional lead anchors, can be delivered with the lead through an introducer during the implantation process. The lead anchoring elements extend into, and lodge against, patient tissue and prevent or reduce lateral or axial (or both lateral and axial) migration of the lead after implantation. The lead anchoring elements can be particularly useful for leads for sacral nerve stimulation, spinal cord stimulation, or the stimulation of other patient tissue and organs. Although the anchoring elements are illustrated below for use with a lead, it will be understood that the same anchoring elements can be used with a lead extension. Moreover, where the discussion below describes electrodes of the lead, the corresponding element in a lead extension would be the connector or connector contacts of the lead extension.

FIG. 4A illustrates one embodiment of a portion of a lead with a lead body 406, an electrode 434, and three anchoring elements 450 each extending out of an open slot 458 in the lead body. Each of the anchoring elements 450 includes a first end portion 452 disposed in an anchoring lumen 456 (see, also, FIG. 4B) within the lead body 406 and a second end portion 454 for contacting tissue and anchoring the lead within the tissue. In at least some embodiments, each of the anchoring elements 450 is associated with a different open slot 458 and anchoring lumen 456.

Each anchoring element 450 has a thin, elongate structure and can be made of, for example, a conductive or non-conductive wire. Suitable wires include, but are not limited to, those having a diameter of no more than 0.1 mm, 0.2 mm, 0.25 mm, 0.3 mm, 0.4 mm, or 0.5 mm. The anchoring element can have any suitable length. In at least some embodiments, the anchoring element 450 has a length of at least 0.4 mm, 0.5 mm, 1 mm, 2.5 mm, 5 mm, 10 mm, 12 mm, or 15 mm outside of the lead body 406 when extended away from the lead body. In at least some embodiments, the anchoring element 450 has a length of at least 1 mm, 2.5 mm, 5 mm, 10 mm, 15 mm, 20 mm, or 25 mm within an anchoring lumen of the lead body 406 when the second end portion 454 extends away from the lead body.

In at least some embodiments, the anchoring element 450 is made of a material with superelastic properties such as, but not limited to, Nitinol™. In at least some embodiments, the anchoring element 450 is made of a shape memory material such as, but not limited to, Nitinol™. A shape memory material has a preferred configuration that can be set by a user or manufacturer or the like. As an example, at least some shape memory materials can be heated, positioned in the preferred configuration, and then cooled to set the desired preferred configuration. A superelastic material also has a preferred configuration.

The superelastic or shape memory material remains in the preferred configuration unless a force is applied to change the configuration. When the force is removed, the superelastic or shape memory material returns (or attempts to return) to the preferred configuration. For example, the anchoring elements 450 can be formed of a Ni—Ti alloy (such as Nitinol™) with shape memory and superelastic properties and can be deployed by heating the anchoring element above the transformation temperature (referred to as Austenite finish transformation temperature for Ni—Ti (e.g., Nitinol™) alloys). Above the transformation temperature, anchoring elements recover to their preferred configuration (e.g., a deployed state), and below the transformation temperature, anchoring elements will be in their constrained state. In at least some embodiments, the transformation temperature is between room temperature (20° C.) and body temperature (37° C.). Anchoring elements can also be constrained against the lead body or within the exposed lumen 458 by a sheath.

In at least some embodiments, the preferred configuration is a deployed configuration in which the second end portion 454 of the anchoring element 450 extends away from the lead body 406 and into the tissue in which the lead is implanted. In at least some embodiments, the second end portion 454 of the anchoring element 450 has a hook or curved shape, as illustrated in FIG. 4A, in the deployed configuration. Examples of other shapes for the second end portion 454 include, but are not limited to, a straight, tine-like shape (see, for example, FIG. 6B) where the second end portion extends straight away from the lead body at a selected angle with respect to the lead body, as explained in more detail below.

The anchoring element 450 resists changing from the preferred configuration, but the anchoring element can be constrained by, for example, an introducer (e.g., a needle, sheath, cannula, or other introducer) to lie against or within the lead body 406 (e.g., within the anchoring lumen 456 or open slot 458) as the lead is implanted into the body of the patient. This retracted or constrained configuration is useful for implantation to reduce the overall diameter of the lead to no greater than the inner diameter of the introducer. When the introducer is removed, the anchoring element 450 returns (or attempts to return) to the preferred configuration (e.g., the deployed configuration) with, for example, the second end portion 454 extending away from the lead body 406.

In at least some embodiments, the open slots 458 and anchoring lumens 456 can be sufficiently long so that the anchoring elements 450 can lie entirely within the anchoring lumens 456 when constrained in an introducer or the like. In other embodiments, a portion of the anchoring element 450 may remain outside the anchoring lumen 456 when constrained if, for example, the open slot 458 or anchoring lumen 456 is not sufficiently long to accommodate the entire second end portion 454 of the anchoring element.

In at least some embodiments, to explant or remove the lead from patient tissue, a sheath, needle, or cannula (or the like) can be slid over the lead constraining the anchoring elements 450 to lie against or within the lead body 406 so that the lead can be explanted or removed.

The first end portion 452 lies within the anchoring lumen 456. The first end portion 452 can be frictionally held within the anchoring lumen 456 or can be held using adhesive (for example, epoxy), back-filled polymer material, flow of the polymer material of the lead body around the first end portion by heating the lead body, heat shrink material within the lead body or as part of the lead body, or any other securement mechanism or any combination of these securement mechanisms.

In some embodiments, the anchoring lumens 456 can extend along the entire length of the lead body. Alternatively, the anchoring lumens 456 may only extend along a portion of the lead body, for example, near the distal end of the lead body where the anchoring elements are positioned. In some embodiments, the portion of the anchoring lumen 456 distal to the open slot 458 may be filled with polymer material, such as the polymer that forms the lead body or epoxy or any other suitable material, prior to or after insertion of the anchoring element 450 into the anchoring lumen 456. This can seal the anchoring lumen distal to the open slot. In other embodiments, the anchoring lumen 456 may terminate with the open slot 458

In the embodiment illustrated in FIG. 4A, the first end portion 452 of the anchoring element 450 is disposed in the portion of the anchoring lumen 450 that is proximal to the open slot 458. In other embodiments, (see, for example, FIGS. 7A-7B) the first end portion of the anchoring element is disposed in the portion of the anchoring lumen that is distal to the open slot. It will be recognized that for embodiments having more than one anchoring element, the anchoring elements can all extend from the portion of the anchoring lumen proximal to the open slot (e.g., FIG. 4A) or all from the portion of the anchoring lumen distal to the open slot (e.g., FIGS. 7A-7B) or some from the proximal portion and some from the distal portion.

In the embodiment illustrated in FIG. 4A, the second end portions 454 of the anchoring elements 450 extend toward the proximal end of the lead. It will be understood that in other embodiments, the second end portions may extend toward the distal end of the lead or that some of the second end portions may extend toward the proximal end of the lead and others may extend toward the distal end of the lead. Moreover, in some embodiments, one or more of the anchoring elements may extend perpendicularly outward from the lead body and not extend toward either the proximal or distal part of the lead.

Any number of anchoring elements 450 can be used. For example, a lead can have one, two, three, four, five, six, eight, nine, ten, twelve, or more anchoring elements. The illustrated embodiment has three anchoring elements 450. Moreover, in at least some embodiments, the anchoring elements can be arranged in sets with each set disposed at a same longitudinal position along the lead and having two or more anchoring elements 450 disposed about the circumference of the lead body 406. The illustrated embodiment has one set of three anchoring elements 450, but other embodiments can have two, three, four, five, six, or more sets of anchoring elements. The anchoring elements in a set can be distributed uniformly or non-uniformly about the circumference of the lead body. The sets can also be distributed with uniform or non-uniform spacing between sets and the anchoring elements of one set can be aligned with those of another set(s) or can be offset. The sets can have the same number of anchoring elements or can have different numbers of anchoring elements.

The illustrated embodiment provides the anchoring elements 450 proximal to the electrode 434. In some embodiments, some or all of the anchoring elements are proximal to all of the electrodes. In some embodiments, some or all of the anchoring elements are distal to all of the electrodes. In some embodiments, one or more of the anchoring elements are positioned between the electrodes. For embodiments having more than one anchoring element, any combination of positioning of the individual anchoring elements (e.g., proximal to, distal to, or between the electrodes) can be used.

In at least some embodiments, the lead body 406 includes a multi-lumen tubing 460 that defines the anchoring lumens 456 and one or more conductor lumens 462 for passage of the conductors along the lead between the electrodes and the terminals, as illustrated in FIGS. 4B and 4C. In some embodiments, the multi-lumen tubing 460 may include a central lumen for a stylet during implantation or for passage of drugs or fluids through the lead to the treatment site. The multi-lumen tubing 460 can be made from any suitable biocompatible (preferably, non-conductive) material including, but not limited to, silicone, polyurethane, or the like or combinations thereof. Preferably, the multi-lumen tubing 460 is flexible. In some embodiments, the conductor lumens 462 each carry a single conductor. In other embodiments, a conductor lumen may hold more than one conductor.

The open slots 458 can be formed by any suitable method including, but not limited to, removing a portion of the multi-lumen tubing 460 separating the corresponding anchoring lumen 456 from the exterior of the multi-lumen tubing, as illustrated in FIG. 4C. The removal of material of the multi-lumen tubing to form the open slots can be performed by any suitable method including, but not limited to, ablation, cutting, grinding, or the like.

FIGS. 5A and 5B illustrate, in cross-section, a portion of another embodiment of a lead having a lead body 506 and anchoring elements 550 disposed in anchoring lumens 556 with open slots 558 for deployment of the anchoring elements (see. FIG. 5B.) In this embodiment, the anchoring elements 550 are deployed from a retracted position (FIG. 5A) to a deployed position (FIG. 5B) by pushing the anchoring elements 550 along the anchoring lumens 556 and out the open slots 558. A mechanism (not shown) may be provided at the proximal end of the lead or external to the lead for the user to manually deploy or retract the anchoring elements 550. The mechanism can be as simple as the anchoring elements extending outside the lead for the user to push or pull or the mechanism can be a sliding mechanism that is attached the anchoring elements or any other suitable mechanism. After the introducer needle is removed, the sheath can keep the anchors in the un-deployed state until it is removed. All of the design considerations, including materials, orientation, positioning, and dimensions, described above for the embodiment of FIG. 4A can be implemented in this embodiment, unless indicated otherwise. For example, the anchoring elements 550 can be made of shape memory material that forms a hook when the anchoring element is deployed outside the anchoring lumen, as illustrated in FIG. 5B.

FIGS. 6A and 6B illustrate, in cross-section, a portion of another embodiment of a lead having a lead body 606 and anchoring elements 650 disposed in anchoring lumens 656 with open slots 658 for deployment of the anchoring elements (see. FIG. 6B.) All of the design considerations, including materials, orientation, positioning, and dimensions, described above for the embodiments of FIGS. 4A, 5A, and 5B can be implemented in this embodiment, unless indicated otherwise.

In this embodiment, the second end portion 654 of the anchoring element 650, when deployed, has a straight, tine-like configuration which makes an angle 664 with respect to the lead body 606, as illustrated in FIG. 6B. In the illustrated embodiment of FIG. 6B, the angle 664 is ninety degrees. In other embodiments, the angle is in a range from 85 to 95 degrees or in a range from 80 to 100 degrees or in a range from 75 to 105 degrees or in a range from 60 to 120 degrees or in a range from 45 to 135 degrees or in a range from 30 to 140 degrees or in a range from 10 to 170 degrees. In yet other embodiments, the angle is less than 90 degrees or in a range from 85 to 90 degrees or in a range from 75 to 90 degrees or in a range from 60 to 90 degrees or in a range from 45 to 90 degrees or in a range from 30 to 90 degrees or in a range from 10 to 90 degrees. In yet other embodiments, the angle is more than 90 degrees or in a range from 90 to 95 degrees or in a range from 90 to 105 degrees or in a range from 90 to 120 degrees or in a range from 90 to 135 degrees or in a range from 90 to 150 degrees or in a range from 90 to 170 degrees. Angles less than 90 degrees may further increase resistance to movement in the proximal direction and angle greater than 90 degrees may further increase resistance to movement in the distal direction.

Figure 7A:
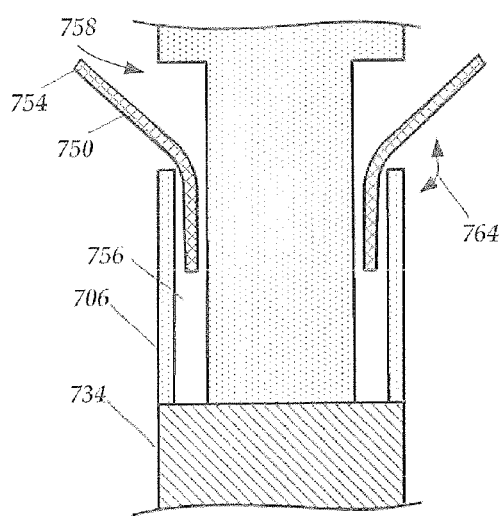
FIG. 7A is a schematic longitudinal cross-sectional view of a portion of one embodiment of a lead with anchoring elements, according to the invention.
Figure 7B:
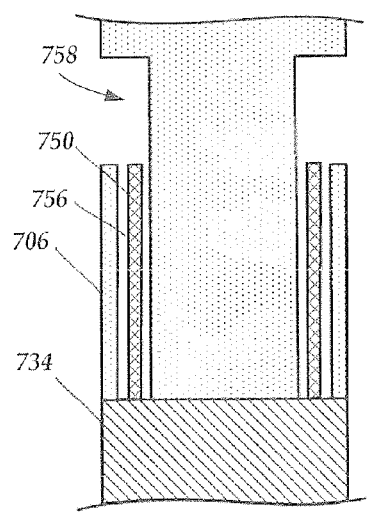
FIG. 7B is a schematic longitudinal cross-sectional view of the portion of the lead of FIG. 7A with the anchoring elements retracted, according to the invention.

FIGS. 7A and 7B illustrate, in cross-section, a portion of another embodiment of a lead having a lead body 706, an electrode 734, and anchoring elements 750 disposed in anchoring lumens 756 with open slots 758 for deployment of the anchoring elements, as illustrated in FIG. 7B. The second end portion 754 of the anchoring element 750, when deployed, has a straight, tine-like configuration which makes an angle 764 with respect to the lead body 706, as illustrated in FIG. 7B. All of the design considerations, including materials, orientation, positioning, angles, and dimensions, described above for the embodiments of FIGS. 4A, 5A, 5B 6A, and 6B can be implemented in this embodiment, unless indicated otherwise.

In this embodiment, the anchoring elements 750 are retractable back into the anchoring lumen 756, as illustrated in FIG. 7B. The anchoring elements 750 can anchor the lead within patient tissue, but when the lead is manually pulled proximally (for example, to remove or explant the lead), the anchoring elements 750 retract back into the anchoring lumens 756 or open slots 758. In at least some embodiments, the deployed second end portions 754 (see, FIG. 7A) of the anchoring elements 750 can be constrained within an introducer to lie next to the lead body 706 during implantation. When the introducer is removed the anchoring elements 750 extend away from the lead body in the deployed configuration illustrated in FIG. 7A.

Figure 8A:
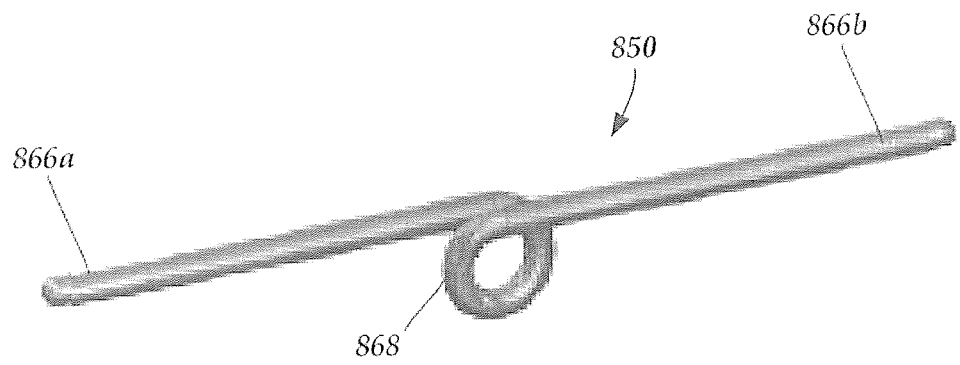
FIG. 8A is a schematic perspective view of a wrapped anchoring element, according to the invention.
Figure 8B:
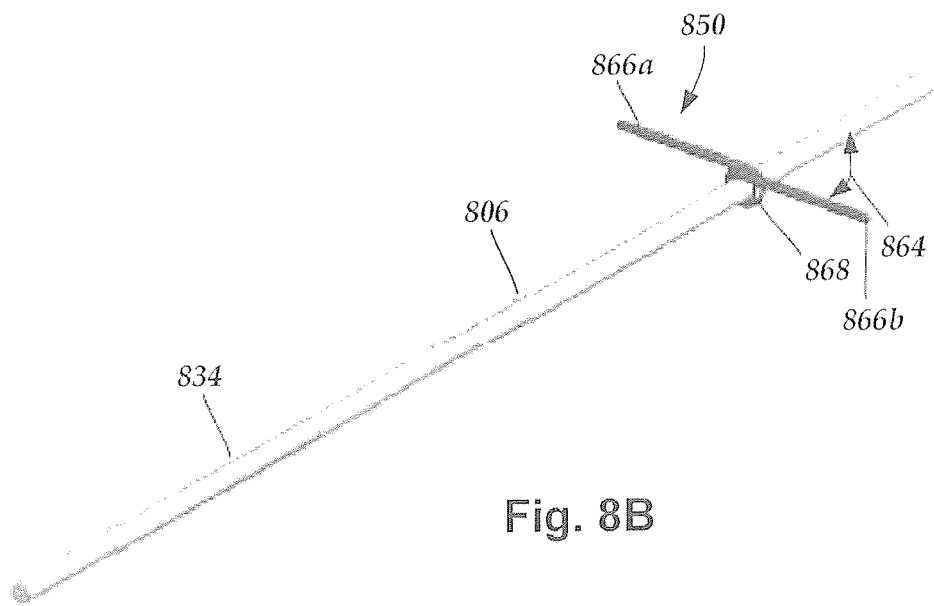
FIG. 8B is a schematic perspective view of a portion of one embodiment of a lead with the wrapped anchoring element of FIG. 8A disposed on the lead body, according to the invention.

FIGS. 8A and 8B illustrate a wrapped anchoring element 850 disposed on the lead body 806 of a lead that also includes one or more electrodes 834. The wrapped anchoring element 850 includes two ends 866a, 866b and a mounting section 868 that is wrapped around the lead body 806 to form one or more coils.

Each anchoring element 850 has a thin, elongate structure and can be made of, for example, a conductive or non-conductive wire. Suitable wires include, but are not limited to, those having a diameter of no more than 0.1 mm, 0.2 mm, 0.25 mm, 0.3 mm, 0.4 mm, or 0.5 mm. The anchoring element can have any suitable length. In at least some embodiments, each end 866a, 866b of the anchoring element 850 has a length of at least 0.4 mm, 0.5 mm, 1 mm, 2.5 mm, 5 mm, 10 mm, 12 mm, or 15 mm extending away from the lead body.

In at least some embodiments, the anchoring element 850 is made of a material with superelastic properties such as, but not limited to, Nitinol™. In at least some embodiments, the anchoring element 850 is made of a shape memory material such as, but not limited to, Nitinol™. A shape memory material has a preferred configuration that can be set by a user or manufacturer or the like. As an example, at least some shape memory materials can be heated, positioned in the preferred configuration, and then cooled to set the desired preferred configuration. A superelastic material also has a preferred configuration.

The superelastic or shape memory material remains in the preferred configuration unless a force is applied to change the configuration. When the force is removed, the superelastic or shape memory material returns (or attempts to return) to the preferred configuration. For example, the anchoring elements 850 can be formed of a Ni—Ti alloy (such as Nitinol™) with shape memory and superelastic properties and can be deployed by heating the anchoring element above the transformation temperature (referred to as Austenite finish transformation temperature for Ni—Ti (e.g., Nitinol™) alloys). Above the transformation temperature, anchoring elements recover to their preferred configuration (e.g., a deployed state), and below the transformation temperature, anchoring elements will be in their constrained state. In at least some embodiments, the transformation temperature is between room temperature (20° C.) and body temperature (37° C.). Anchoring elements can also be constrained against the lead body or within the exposed lumen 458 by a sheath.

The anchoring element 850 resists changing from the preferred configuration with the ends 866a, 866b extended, but the anchoring element can be constrained by, for example, an introducer (e.g., a needle, sheath, cannula, or other introducer) to lie against the lead body 806 as the lead is implanted into the body of the patient. This constrained configuration is useful for implantation to reduce the overall diameter of the lead to no greater than the inner diameter of the introducer. When the introducer is removed, the anchoring element 850 returns (or attempts to return) to the preferred configuration (e.g., the deployed configuration.)

In the illustrated embodiment, each end 866a, 866b extends perpendicularly away from the lead body 806, but in other embodiments, an angle 864 between an end 866a. 866b and the lead body 806 may be more or less than 90 degrees. Moreover, the two ends 866a, 866b may, but do not necessarily, extend at the same angle from the lead body 806. In other embodiments, the angle is in a range from 85 to 95 degrees or in a range from 80 to 100 degrees or in a range from 75 to 105 degrees or in a range from 60 to 120 degrees or in a range from 45 to 135 degrees. In yet other embodiments, the angle is less than 90 degrees or in a range from 85 to 90 degrees or in a range from 75 to 90 degrees or in a range from 60 to 90 degrees or in a range from 45 to 90 degrees or in a range from 30 to 90 degrees. In yet other embodiments, the angle is more than 90 degrees or in a range from 90 to 95 degrees or in a range from 90 to 105 degrees or in a range from 90 to 120 degrees or in a range from 90 to 135 degrees or in a range from 90 to 150 degrees.

Any number of anchoring elements 450 can be used. For example, a lead can have one, two, three, four, five, six, eight, nine, ten, twelve, or more anchoring elements. The illustrated embodiment provides the anchoring elements 850 proximal to the electrode 834. In some embodiments, some or all of the anchoring elements are proximal to all of the electrodes. In some embodiments, some or all of the anchoring elements are distal to all of the electrodes. In some embodiments, one or more of the anchoring elements are positioned between the electrodes. For an embodiment with more than one of the anchoring elements 850, any combination of positioning of the anchoring elements (e.g., proximal to, distal to, or between) can be used. Also, for any embodiment with more than one of the anchoring elements 850, the respective ends 866a, 866b of the individual anchoring elements may extend in the same direction, respectively, or they may extend in different directions or at different angles.

Figure 9:
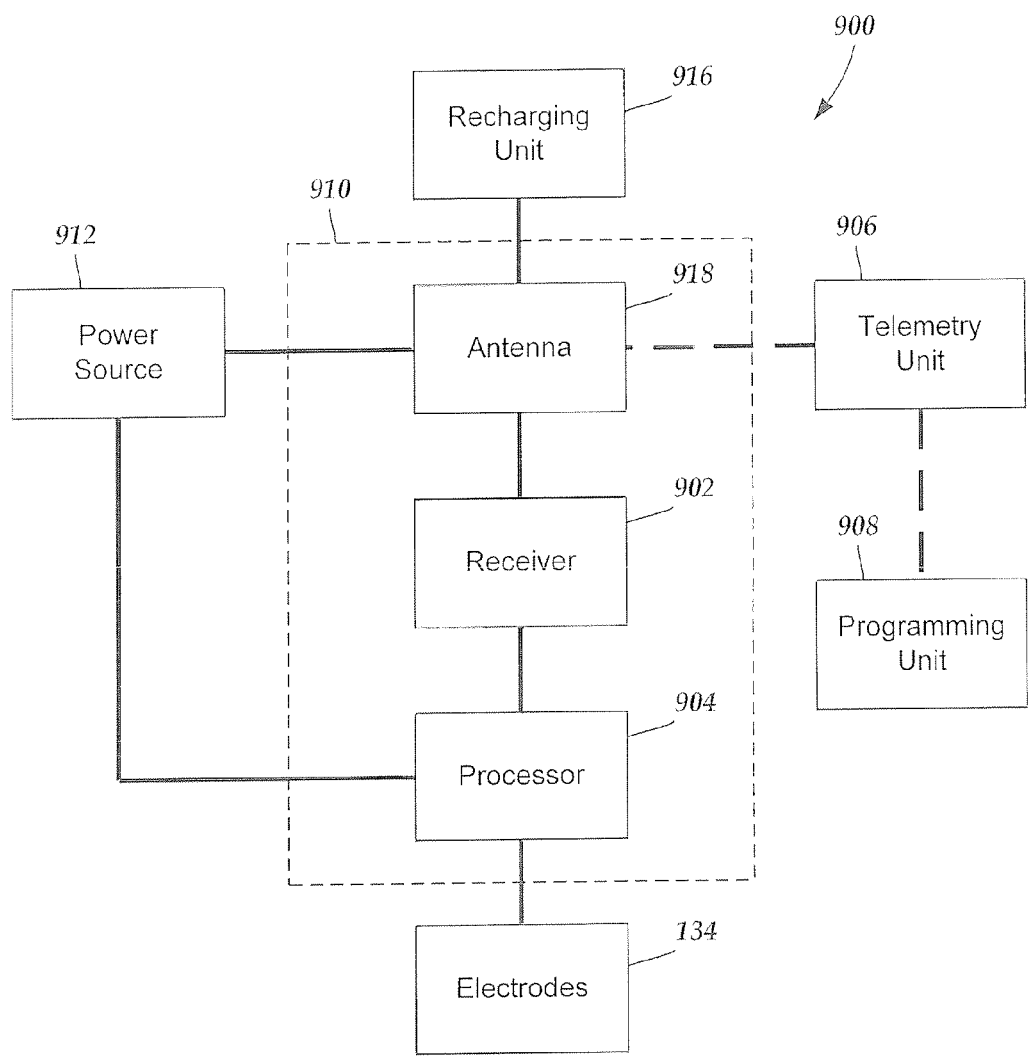
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
    at least one lead body having a distal end portion, a proximal end portion, and a longitudinal length, wherein the lead body defines at least one anchoring lumen extending longitudinally along at least a portion of the lead body and at least one open slot extending longitudinally along the lead body, wherein each anchoring lumen has a distal end portion and a proximal end portion, wherein the distal end portion of the anchoring lumen is exposed by the at least one open slot associated with the anchoring lumen;
    at least one electrode disposed along the distal end portion of the at least one lead body;
    at least one terminal disposed along the proximal end portion of the at least one lead body;
    at least one conductor electrically coupling the at least one terminal to the at least one electrode;
    at least one thin, elongate anchoring element having a distal end portion and a proximal end portion, each of the distal end portion and the proximal end portion having a longitudinal length, wherein, for each anchoring element, the proximal end portion of the anchoring element is disposed in the proximal end portion of a one of the at least one anchoring lumen and the distal end portion of the anchoring element is configured and arranged preferentially to extend out of the open slot associated with the one of the at least one anchoring lumen and away from the lead body in a deployed configuration unless the distal end portion of the anchoring element is constrained in a constrained configuration with the distal end portion of the anchoring element lying in the distal end portion of the one of the at least one anchoring lumen and completely exposed by the open slot associated with the one of the at least one anchoring lumen.

2. The electrical stimulation lead of claim 1, wherein, in the deployed configuration, each of the at least one anchoring element forms a hook.

3. The electrical stimulation lead of claim 1, wherein, in the deployed configuration, each of the at least one anchoring element forms a tine extending straight out of the anchoring lumen.

4. The electrical stimulation lead of claim 3, wherein, in the deployed configuration, each of the at least one anchoring element extends perpendicularly from the lead body.

5. The electrical stimulation lead of claim 3, wherein, in the deployed configuration, each of the at least one anchoring element extends at an angle in a range of 10 to 170 degrees relative to the lead body.

6. The electrical stimulation lead of claim 1, wherein the lead body comprises a multi-lumen tubing defining the at least one anchoring lumen and one or more conductor lumens.

7. The electrical stimulation lead of claim 1, wherein the distal end portion of the at least one anchoring element is constrained in a constrained configuration adjacent to or within the lead body using an introducer.

8. The electrical stimulation lead of claim 1, wherein the at least one anchoring element is formed of a superelastic material configured and arranged to change from the constrained configuration to the deployed configuration by heating the anchoring element above a transformation temperature which is a temperature below body temperature.

9. The electrical stimulation lead of claim 1, wherein the at least one anchoring element is formed of a superelastic material configured and arranged to change from the constrained configuration to the deployed configuration by heating the anchoring element above a transformation temperature which is a temperature between room temperature and body temperature.

10. The electrical stimulation lead of claim 1, wherein the lead body comprises a multi-lumen tubing defining the at least one anchoring lumen and a central lumen separate from the at least one anchoring lumen.

11. An electrical stimulating system comprising:
    the electrical stimulation lead of claim 1; and
    a control module coupleable to the electrical stimulation lead.

12. An electrical stimulation lead, comprising:
    at least one lead body having a distal end portion, a proximal end portion, and a longitudinal length;
    at least one electrode disposed along the distal end portion of the at least one lead body;
    at least one terminal disposed along the proximal end portion of the at least one lead body;
    at least one conductor electrically coupling the at least one terminal to the at least one electrode; and
    at least one thin, elongate anchoring element having a first end and a second end, wherein the lead body defines at least one anchoring lumen extending longitudinally along at least a portion of the lead body and at least one open slot extending along the longitudinal length of the lead body and open along the longitudinal length, wherein each of the at least one anchoring lumen is open at one of the at least one open slot associated with the anchoring lumen, wherein, for each anchoring element, the first end of the anchoring element is disposed in one of the at least one anchoring lumen and the second end of the anchoring element is configured and arranged preferentially to extend out of the open slot associated with the anchoring lumen and away from the lead body in a deployed configuration unless the second end is constrained in a constrained configuration adjacent or within the lead body, wherein the at least one anchoring element is formed of a superelastic material configured and arranged to change from the constrained configuration to the deployed configuration by heating the anchoring element above a transformation temperature which is a temperature below body temperature.

13. The electrical stimulation lead of claim 12, wherein, unless constrained, the second end of each anchoring element extends at an angle in a range from 10 to 170 degrees relative to the lead body.

14. The electrical stimulation lead of claim 12, wherein the lead is configured and arranged for retraction of the at least one anchoring element by application of at least a predetermined amount of pulling force to the lead when the lead is implanted.

15. The electrical stimulation lead of claim 12, wherein the transformation temperature is between room temperature and body temperature.

16. The electrical stimulation lead of claim 12, wherein the lead body comprises a multi-lumen tubing defining the at least one anchoring lumen and one or more conductor lumens.

17. The electrical stimulation lead of claim 12, wherein the lead body comprises a multi-lumen tubing defining the at least one anchoring lumen and a central lumen separate from the at least one anchoring lumen.

18. An electrical stimulating system comprising:
   the electrical stimulation lead of claim 12; and
   a control module coupleable to the electrical stimulation lead.

\* \* \* \* \*